United States Patent
Glik et al.

(10) Patent No.: US 11,857,260 B2
(45) Date of Patent: Jan. 2, 2024

(54) RETINAL CAMERAS HAVING MOVABLE OPTICAL STOPS

(71) Applicant: Verily Life Sciences LLC, Mountain View, CA (US)

(72) Inventors: Eliezer Glik, San Francisco, CA (US); Sam Kavusi, Menlo Park, CA (US); Ryan Kramer, San Francisco, CA (US); Todd Whitehurst, Belmont, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 288 days.

(21) Appl. No.: 16/649,437

(22) PCT Filed: Sep. 19, 2018

(86) PCT No.: PCT/US2018/051826
§ 371 (c)(1),
(2) Date: Mar. 20, 2020

(87) PCT Pub. No.: WO2019/060467
PCT Pub. Date: Mar. 28, 2019

(65) Prior Publication Data
US 2020/0237214 A1    Jul. 30, 2020

Related U.S. Application Data

(60) Provisional application No. 62/561,530, filed on Sep. 21, 2017.

(51) Int. Cl.
*A61B 3/10* (2006.01)
*A61B 3/113* (2006.01)
(Continued)

(52) U.S. Cl.
CPC ............. *A61B 3/14* (2013.01); *A61B 3/113* (2013.01); *A61B 3/12* (2013.01); *G02F 1/1334* (2013.01)

(58) Field of Classification Search
CPC ......... A61B 3/1025; A61B 3/02; A61B 3/102; A61B 3/113; A61B 3/1015; A61B 3/12;
(Continued)

(56) References Cited

U.S. PATENT DOCUMENTS

| 4,238,142 A | 12/1980 | Grolman et al. |
| 4,881,808 A | 11/1989 | Bille et al. |

(Continued)

FOREIGN PATENT DOCUMENTS

| CN | 1977762 A | 6/2007 |
| CN | 101268928 A | 9/2008 |

(Continued)

OTHER PUBLICATIONS

Extended European Search Report dated Jun. 9, 2021 for EP Application 18859631.6, 10 pages.

(Continued)

*Primary Examiner* — Dawayne Pinkney
(74) *Attorney, Agent, or Firm* — Perkins Coie LLP

(57) ABSTRACT

Introduced here are retinal cameras having optical stops whose size and/or position can be modified to increase the size of the space in which an eye can move while being imaged. In some embodiments, an optical stop is mechanically moved to recover retinal image quality as the subject shifts their eye. In some embodiments, an optical stop is digitally created using a pixelated liquid crystal display (LCD) layer having multiple pixels that are individually controllably. In some embodiments, multiple non-pixelated LCD layers are connected to one another to form a variable transmission stack, and each LCD layer within the variable (Continued)

transmission stack may be offset from the other LCD layers. In such embodiments, the optical stop can be moved by changing which LCD layer is active at a given point in time.

11 Claims, 13 Drawing Sheets

(51) Int. Cl.
*A61B 3/12* (2006.01)
*A61B 3/02* (2006.01)
*A61B 3/14* (2006.01)
*G02F 1/1334* (2006.01)

(58) Field of Classification Search
CPC ....... A61B 3/1225; A61B 3/024; A61B 3/032; A61B 3/005
USPC ............... 351/206, 200, 205, 209, 210, 214, 351/221–223, 243, 245, 246
See application file for complete search history.

(56) References Cited

U.S. PATENT DOCUMENTS

| | | | |
|---|---|---|---|
| 6,892,030 | B2 | 5/2005 | Rife |
| 6,943,942 | B2 * | 9/2005 | Horiguchi .............. G02B 21/06 |
| | | | 359/383 |
| 2004/0051847 | A1 | 3/2004 | Vilser |
| 2008/0218695 | A1 | 9/2008 | Obrebski |
| 2013/0003593 | A1 | 1/2013 | Bajpay et al. |
| 2013/0208241 | A1 | 8/2013 | Lawson et al. |
| 2015/0362754 | A1 | 12/2015 | Etzkorn et al. |
| 2016/0091739 | A1 * | 3/2016 | He ......................... G02B 5/005 |
| | | | 348/335 |
| 2016/0143528 | A1 | 5/2016 | Wilf et al. |
| 2017/0160548 | A1 | 6/2017 | Woltman et al. |

FOREIGN PATENT DOCUMENTS

| | | | | |
|---|---|---|---|---|
| EP | 2786698 | A1 | 10/2014 | |
| JP | H0591979 | A | 4/1993 | |
| JP | 2004522488 | A | 7/2004 | |
| JP | 2007089828 | A | 4/2007 | |
| JP | 2008049165 | A | 3/2008 | |
| JP | 2011034096 | A | 2/2011 | |
| JP | 2013128800 | A | 7/2013 | |
| JP | 2014200680 | A | 10/2014 | |
| JP | 2016185192 | A | 10/2016 | |
| RU | 2307822 | C2 | 10/2007 | |
| RU | 2607822 | | 1/2017 | |
| RU | 2607822 | C1 | 1/2017 | |
| WO | WO-9966828 | A1 * | 12/1999 | ........... A61B 3/1015 |
| WO | 0205705 | A1 | 1/2002 | |
| WO | WO-2008029634 | A1 * | 3/2008 | ............... A61B 3/12 |
| WO | WO-2015166549 | A1 * | 11/2015 | ............. A61B 3/024 |
| WO | WO-2017025583 | A1 * | 2/2017 | ............. A61B 3/102 |

OTHER PUBLICATIONS

International Search Report and Written Opinion dated Dec. 27, 2018 for PCT Application PCT/US2018/051826, 9 pages.

* cited by examiner

900

901
Subject places eye proximate to the objective lens of a retinal camera

902
Determine location of the eye being imaged by the retinal camera

903
Set the position of an optical stop

904
Generate retinal image from light rays reflected into retinal camera by the eye

905
Monitor position of the eye

906
Modify the position of the optical stop responsive to determining the position of the eye has changed

*FIG. 9*

RETINAL CAMERAS HAVING MOVABLE OPTICAL STOPS

CROSS-REFERENCE TO RELATED APPLICATIONS

This application is a U.S. National Phase Entry of International Application No. PCT/US2018/051826, filed on Sep. 19, 2018, which claims priority to U.S. Provisional Application No. 62/561,530, titled "Retinal Cameras Having Movable Optical Stops" and filed on Sep. 21, 2017, each of which is incorporated by reference herein in its entirety.

TECHNICAL FIELD

Various embodiments concern retinal cameras having optical stops.

BACKGROUND

Fundus photography involves capturing an image of the fundus (i.e., the interior surface of the eye opposite the lens) to document the retina, which is the neurosensory tissue in the eye that translates optical images into the electrical impulses that can be understood by the brain. The fundus can include the retina, optic disc, macula, fovea, and posterior pole.

Retinal cameras (also referred to as "fundus cameras") typically include a microscope and a capturing medium that creates an image from light reflected by the retina. Because the pupil serves as both the entrance point and exit point of light guided toward the retina, the retina can be photographed directly. The structural features that can be identified on a retinal photograph include the central and peripheral retina, optic disc, and macula.

Medical professionals (e.g., optometrists, ophthalmologists, and orthoptists) can use retinal images to monitor the progression of certain diseases and eye conditions. For example, retinal images may be used to document indicators of diabetes, age-macular degeneration (AMD), glaucoma, neoplasm, etc.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 9 depicts a flow diagram of a process for recovering retinal image quality as a subject shifts their eye during the imaging process.

Figure 1:
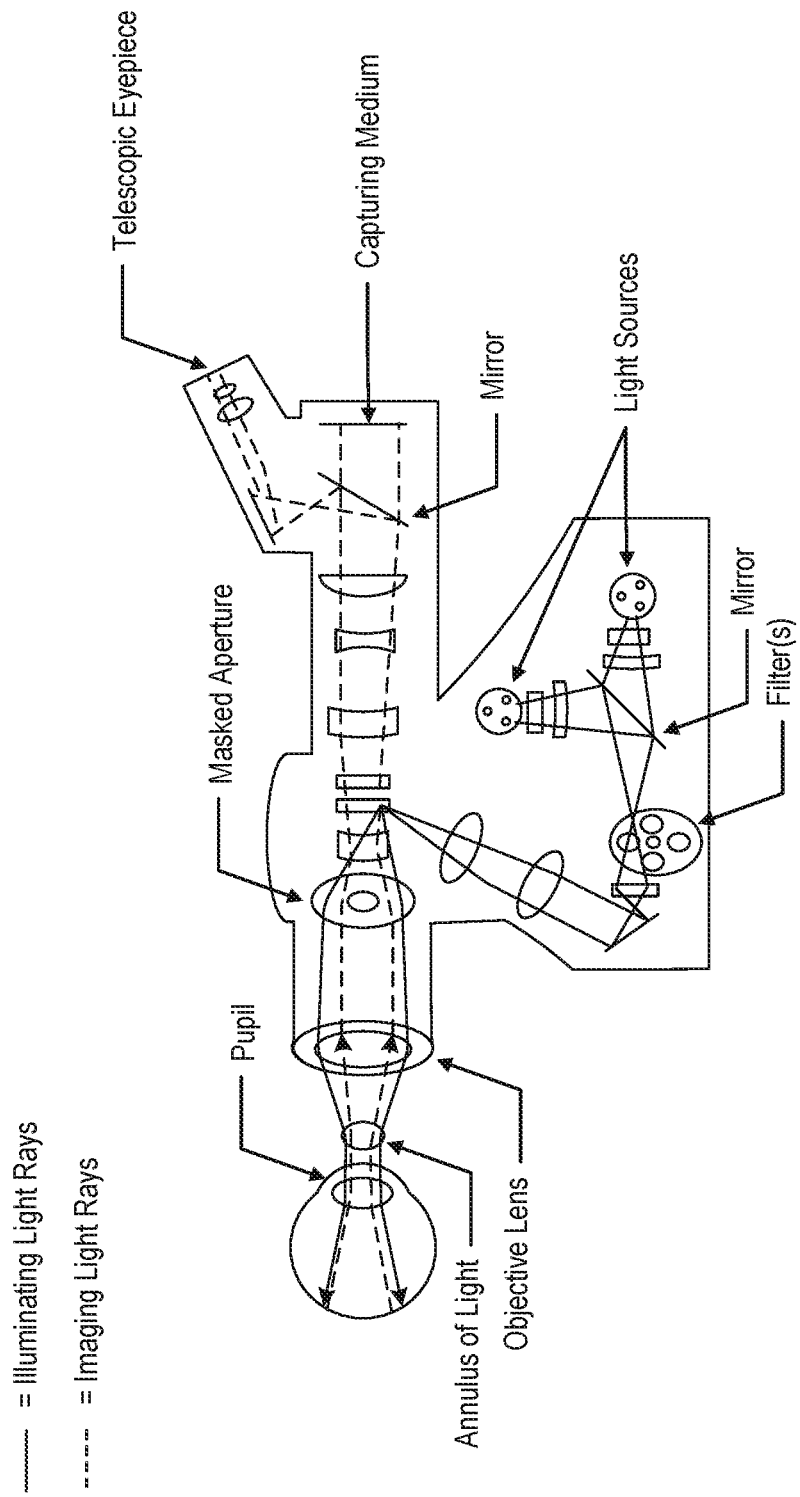
FIG. 1 depicts an example of a retinal camera.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Retinal cameras are designed to provide an upright, magnified view of the fundus. Typically, a retinal camera views 30-50° of the retinal area with a magnification of 2.5×, though these values may be modified using zoom lenses, auxiliary lenses, wide angle lenses, etc.

FIG. 1 depicts an example of a retinal camera. Generally, a subject will sit at the retinal camera with their chin set within a chin rest and their forehead pressed against a bar. An ophthalmic photographer can then visually align the retinal camera (e.g., using a telescopic eyepiece) and press a shutter release that causes an image of the retina to be captured.

More specifically, FIG. 1 illustrates how light can be focused via a series of lenses through a masked aperture to form an annulus that passes through an objective lens and onto the retina. The illuminating light rays are generated by one or more light sources (e.g., light-emitting diodes), each of which is electrically coupled to a power source. When the retina and the objective lens are aligned, light reflected by the retina passes through the un-illuminated hole in the annulus formed by the masked aperture of the retinal camera. Those skilled in the art will recognize that the optics of the retinal camera are similar to those of an indirect ophthalmoscope in that the illuminating light rays entering the eye and the imaging light rays exiting the eye follow dissimilar paths.

The imaging light rays exiting the eye can initially be guided toward a telescopic eyepiece that is used by the ophthalmic photographer to assist in aligning, focusing, etc., the illuminating light rays. When the ophthalmic photographer presses the shutter release, a first mirror can interrupt the path of the illuminating light rays and a second mirror can fall in front of the telescopic eyepiece, which causes the imaging light rays to be redirected onto a capturing medium. Examples of capturing mediums include film, digital charge-coupled devices (CCDs), and complementary metal-oxide-semiconductors (CMOSs). In some embodiments, retinal images are captured using colored filters or specialized dyes (e.g., fluorescein or indocyanine green).

Accordingly, stable alignment of the eye and the retinal camera is critical in capturing high-resolution retinal images. But maintaining such an alignment can be challenging due to the required precision and lack of direct eye gaze control.

Introduced here, therefore, are retinal cameras having optical stops whose size and/or position can be modified to increase the size of the space in which an eye can move while being imaged (also referred to as the "eyebox"). The term "optical stop" refers to the location where light rays entering a retinal camera are traced. Because a retinal camera images light rays reflected back into the retinal camera by the retina, the optical stop is arranged along a plane located inside the retinal camera.

Figure 2:
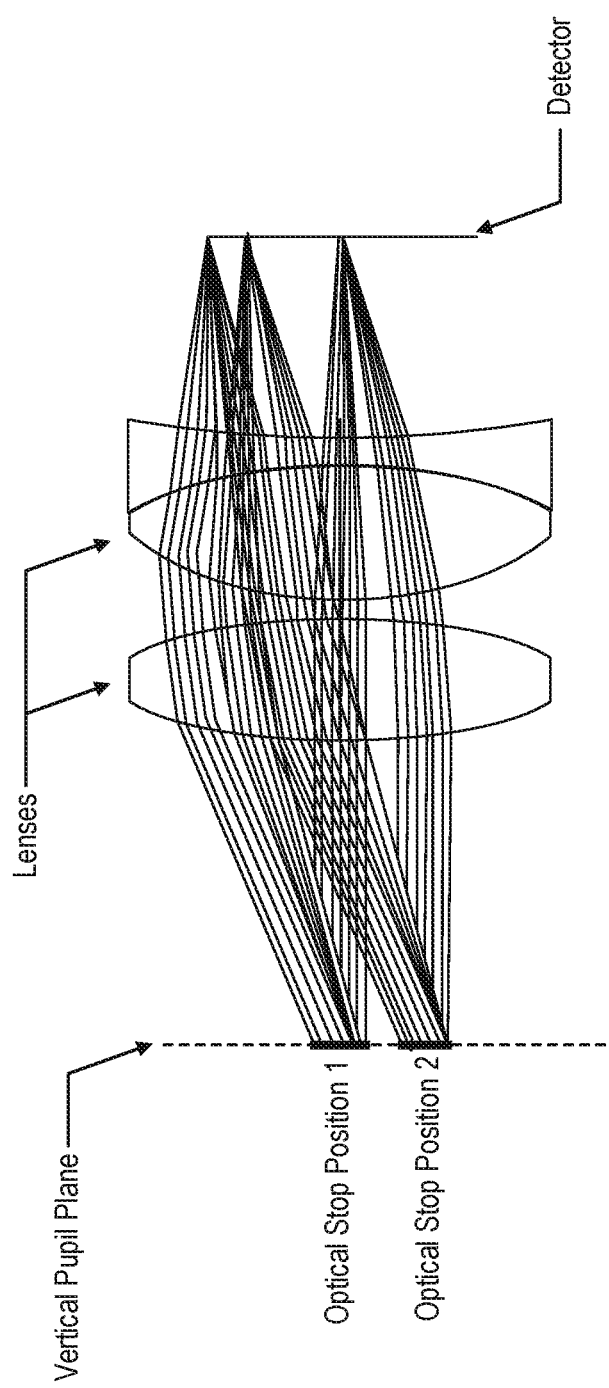
FIG. 2 depicts how moving the eye vertically along the pupil plane may only change the angle of incidence (AOI) of the light rays to the detector of certain eyepieces.

This stands in contrast to other types of eyepieces (e.g., head-mounted devices) where the eye (and, more specifically, the iris) represents the optical stop. For these eyepieces, altering the position of the optical stop does not cause displacement of the light rays along a detector. FIG. 2 depicts how moving the eye vertically along the pupil plane may only change the angle of incidence (AOI) of the light rays to the detector. Here, the first optical stop position represents the optimal eye location (i.e., where the image of the highest quality would be captured) and the second optical stop position represents another position within the eyebox. Because the eye itself acts as the optical stop, a subject can move their eye between the first and second positions without causing vertical or horizontal displacement of the light rays along the detector.

There are several key differences between optical systems having large optical stops and optical systems having smaller optical stops that move to the pupil position. For example, a large optical stop will ensure that an optical system has a small f-number, which is the ratio of the optical system's focal length to the diameter of the entrance pupil. But this can make the optical system more difficult (and more expensive) to construct. A smaller optical stop will limit the amount of light allowed within the imaging space. If the optical stop is smaller than the pupil, then light is lost that would reduce the brightness of the resulting image. Accordingly, it is desirable to make the optical stop substantially the same size as the pupil (e.g., after accounting for magnification). To address movement of the pupil, the retinal cameras introduced here can adjust the position of the optical stop while still maintaining roughly the same diameter as the pupil.

Embodiments may be described with reference to particular imaging configurations, eyepieces, etc. However, those skilled in the art will recognize that the features described herein are equally applicable to other imaging configurations, eyepieces, etc. Moreover, the technology can be embodied using special-purpose hardware (e.g., circuitry), programmable circuitry appropriately programmed with software and/or firmware, or a combination of special purpose hardware and programmable circuitry. Accordingly, embodiments may include a machine-readable medium having instructions that may be used to program a computing device to perform a process for tracking the position of an eye, modifying the position of an optical stop, processing image data to generate a retinal photograph, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling, either direct or indirect, between two or more elements. The coupling/connection can be physical, logical, or a combination thereof. For example, components may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

Alignment is one of the most difficult tasks of retinal imaging. Conventional retinal cameras, for instance, typically require a trained operator, proper securement of the head position, and non-trivial mechanical controls to ensure precise alignment of the eye and imaging components within the retinal camera (e.g., the lenses, optical stop, and detector). Consequently, the eyebox dimensions of conventional retinal cameras are often extremely limited. This makes proper alignment of the eye and the retinal camera difficult, particularly if the subject begins to shift their eye during the imaging process.

Several solutions have been proposed to address the problems posed by small eyeboxes. However, these proposed solutions add mechanical complexity to the retinal camera (and thus increase the cost). Introduced here, therefore, are several different technologies for recovering the eyebox during the imaging process, including:

- A mechanical optical stop that can be moved horizontally and/or vertically to recover retinal image quality as the subject shifts their eye.
- A digital optical stop that can be created using a pixelated liquid crystal display (LCD) layer including multiple pixels that are individually controllable.
- Multiple non-pixelated LCD layers that can be connected to one another to form a stack. Each LCD layer within the stack may be offset from the other LCD layers. Accordingly, the optical stop of the retinal camera can be moved by changing which LCD layer is active at a given point in time.

Each of these technologies is further described below.

Figure 3:
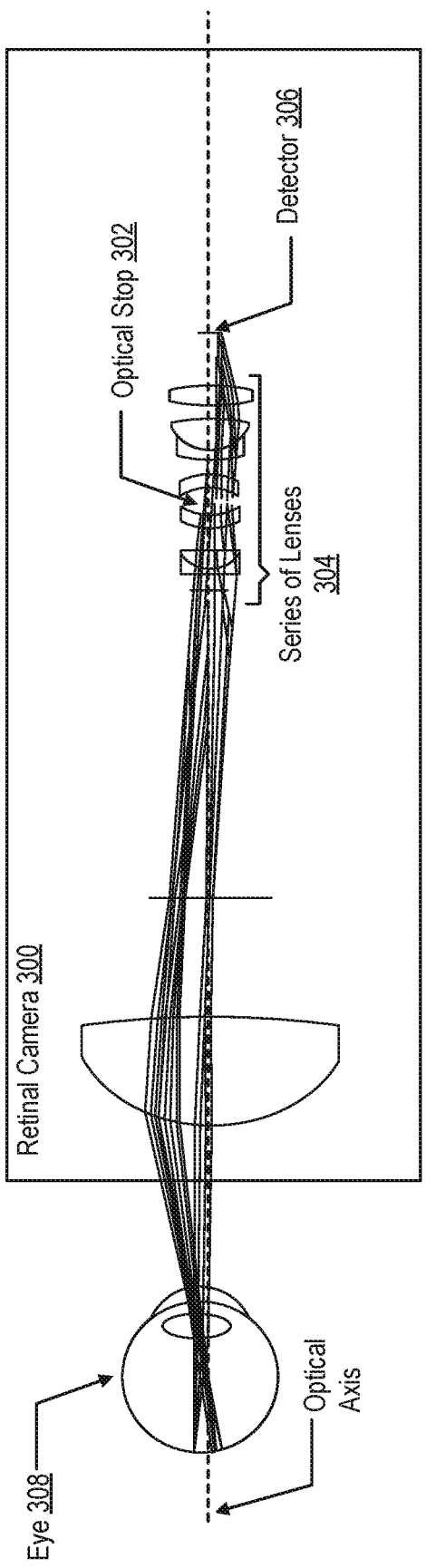
FIG. 3 illustrates a generalized side view of a retinal camera.

FIG. 3 illustrates a generalized side view of a retinal camera 300. Here, the retinal camera 300 includes an optical stop 302 interposed between a series of lenses 304 and a detector 306 (also referred to as a "capturing medium"). Generally, the detector 306 is arranged directly adjacent to the series of lenses 304. Other embodiments of the retinal camera 300 may include some or all of these components, as well as other components not shown here. For example, the retinal camera may include one or more light sources, mirrors for guiding light emitted by the light source(s), a power component (e.g., a battery or a mechanical power interface, such as an electrical plug), a display screen for reviewing retinal images, etc.

As noted above, in some embodiments the optical stop 302 is moved to recover additional light reflected by the eye 308 as the eye 308 moves. Here, for example, the eye 308 has shifted down two millimeters (mm) from the optimal optical axis and the optical stop 302 has shifted down one mm. Such movement allows more of the imaging light rays returning from the eye 308 (e.g., the imaging light rays of FIG. 1) to be guided through the series of lenses 304 and captured by the detector 306.

The relationship between eye shift and optical stop shift may be substantially linear (e.g., approximately two-to-one). Such a relationship allows the proper position of the optical stop 302 to be readily established so long as the position of the eye 308 can be accurately established.

In some embodiments, the optical stop 302 is moved manually. For example, the retinal photographer may visually observe the imaging light rays (e.g., via a telescopic eyepiece) during an imaging session and alter the position of the optical stop 302 using indexing wheel(s), joystick(s), etc.

In other embodiments, the optical stop 302 is moved automatically without requiring input from the retinal photographer or the subject. For example, the retinal camera 300 may instruct servomotor(s) to alter the position of the optical stop 302 responsive to adjustments specified by software executing on the retinal camera 300 or another computing device communicatively coupled to the retinal camera 300. Separate servomotors may be used to alter the position of the optical stop 302 along the x-axis (i.e., horizontally) and the y-axis (i.e., vertically). Other mechanisms may also be used to achieve linear motion of the optical stop 302, including cam(s), stepper motor(s), pneumatic cylinder(s)/actuator(s), piezoelectric actuator(s), voice coil(s), etc.

In some embodiments, movement may occur along a single axis. That is, the optical stop could be restricted to one-dimensional movement (e.g., along the x-axis or the y-axis). For example, movement of the optical stop may be restricted to a curved dimension (e.g., a circular/ellipsoidal path, a rectangular path, or a spiral path).

The software may apply image processing algorithms to identify certain features (e.g., vignetting) that are indicative of increases/decreases in retinal image quality. For example, the software may perform image segmentation (e.g., thresholding methods such as Otsu's method, or color-based segmentation such as K-means clustering) on individual retinal images to isolate features of interest. After the software has identified the retinal image having the highest quality, the software can output instructions that cause the servomotor(s) to modify the position of the optical stop 302. Image quality can depend on one or more factors, such as brightness level, whether vignetting is present, modulation transfer function (MTF) quality, act.

Thus, a subject may be able to look into the retinal camera 300 without being concerned about alignment of the eye 308 and the optical stop 302. Instead, the retinal camera 300 could automatically determine the location of the eye 308 and move the optical stop 302 accordingly. More specifically, the retinal camera 300 may include a mechanism (e.g., a servomotor) operable to reposition the optical stop and a controller configured to adaptively reposition the optical stop responsive to a determination that the eye 308 has moved during the imaging process. For example, the controller may determine the amount of movement caused by a spatial adjustment of the eye, and then cause the mechanism to reposition the optical stop accordingly. As noted above, the amount of movement caused by the spatial adjustment of the eye may be related (e.g., proportional to) the amount by which the optical stop is repositioned. Thus, the optical stop 302 could be moved to ensure alignment with the eye 308, rather than moving the entire retinal camera 300 or the eye 308 itself. In some embodiments, optimized adjustments also occur based on, for example, an image quality feedback loop or some other feedback loop.

Several different mechanisms can be used to detect the location of the eye 308. For example, infrared light source(s) may be arranged to project infrared beam(s) into the visible light illumination path of the retinal camera 300. Because the iris generally does not constrict when illuminated by infrared light, a live view of the retina can be captured and used to establish the position of the eye 308. As another example, the iris may be detected using a software-implemented search pattern. More specifically, the retinal camera 300 could capture a series of retinal images with the optical stop 302 located at different positions. The ideal position for the optical stop 302 may be determined based on whether the retina is detected within any of the retinal images. Other mechanisms for detecting eye location include conventional eye tracking techniques, pupil discover via machine vision, Light Detection and Ranging (LIDAR), radio frequency (RF) object sensing at certain frequencies (e.g., 60 GHz), simple reflection off the cornea, etc.

The optical transfer function (OTF) of an optical system (e.g., a retinal camera) specifies how different spatial frequencies are handled by the optical system. A variant, the modulation transfer function (MTF), neglects phase effects but is otherwise equivalent to the OTF in many instances.

Figure 4A:
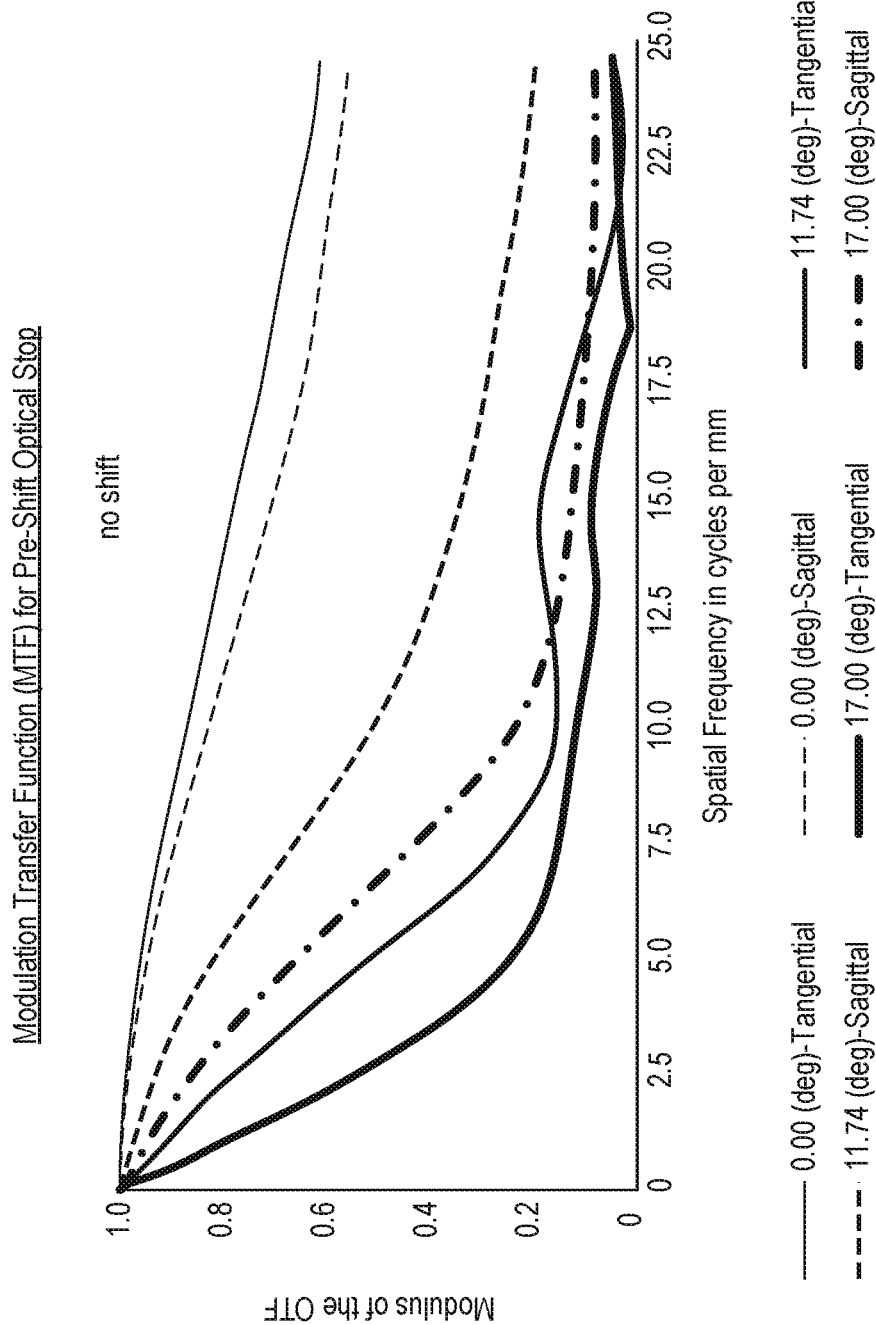
FIG. 4A depicts the modulation transfer function (MTF) of the retinal camera before the optical stop has been shifted.
Figure 4B:
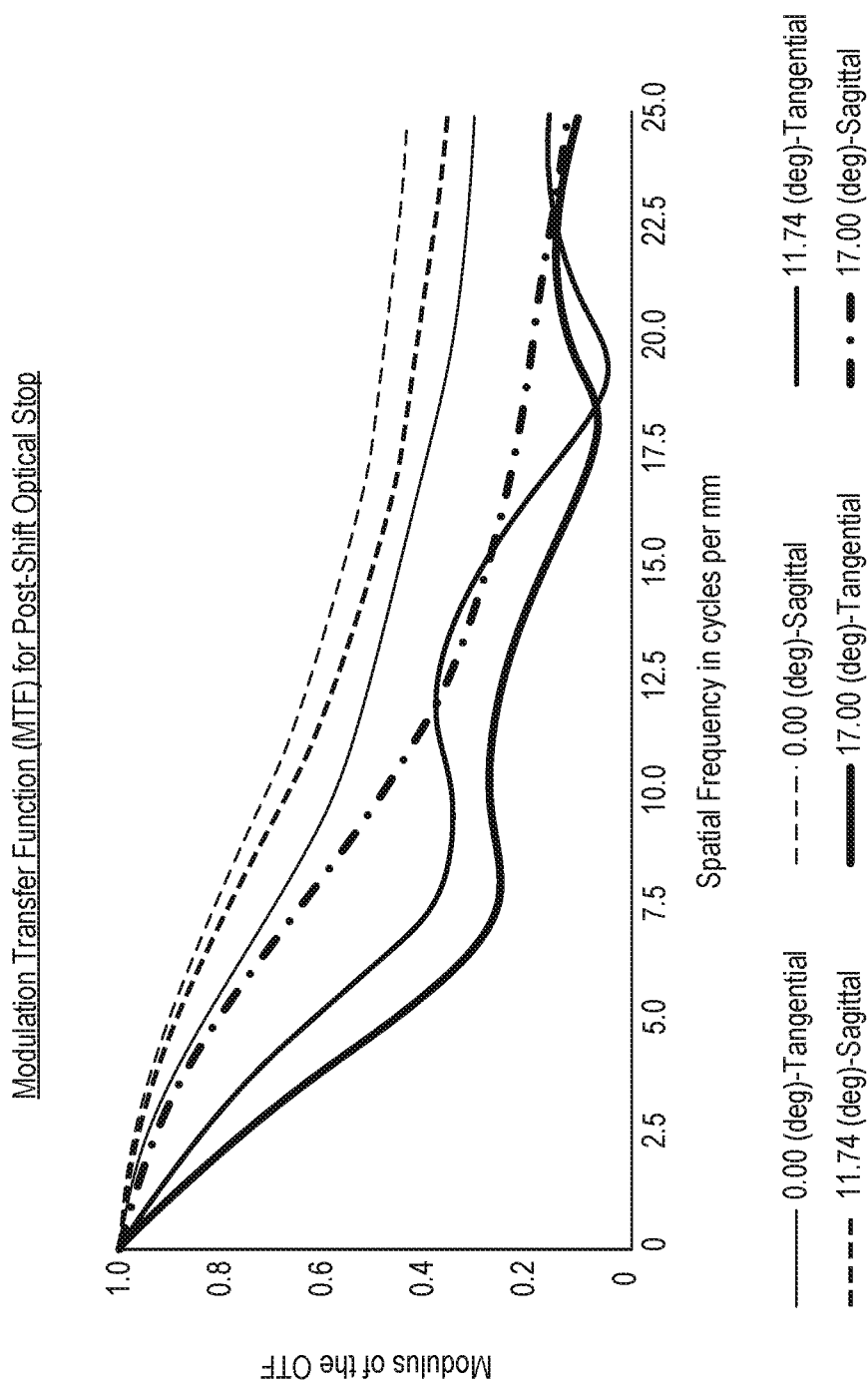
FIG. 4B depicts the MTF of the retinal camera after the optical stop has been shifted.

FIG. 4A depicts the MTF of the retinal camera 300 before the optical stop 302 has been shifted, while FIG. 4B depicts the MTF of the retinal camera 300 after the optical stop 302 has been shifted. Here, the x-axis represents spatial frequency and the y-axis represents modulation.

Each line shown in the MTF represents a different field angle. Lines corresponding to the lowest field angles (i.e., those that are closest to the optimal optical axis) will typically have the highest modulation values, while lines corresponding to the highest field angles (i.e., those that are furthest from the optimal optical axis) will typically have the lowest modulation values. Shifting the optical stop 302 improves retinal image quality by recovering additional light reflected into the retinal camera 300 by the eye 308. Here, for example, the lines corresponding to the high field angles furthest off the optimal optical axis are recovered the most. This is evident in both the increased modulation values and greater definition shown in FIG. 4B.

Figure 5A:
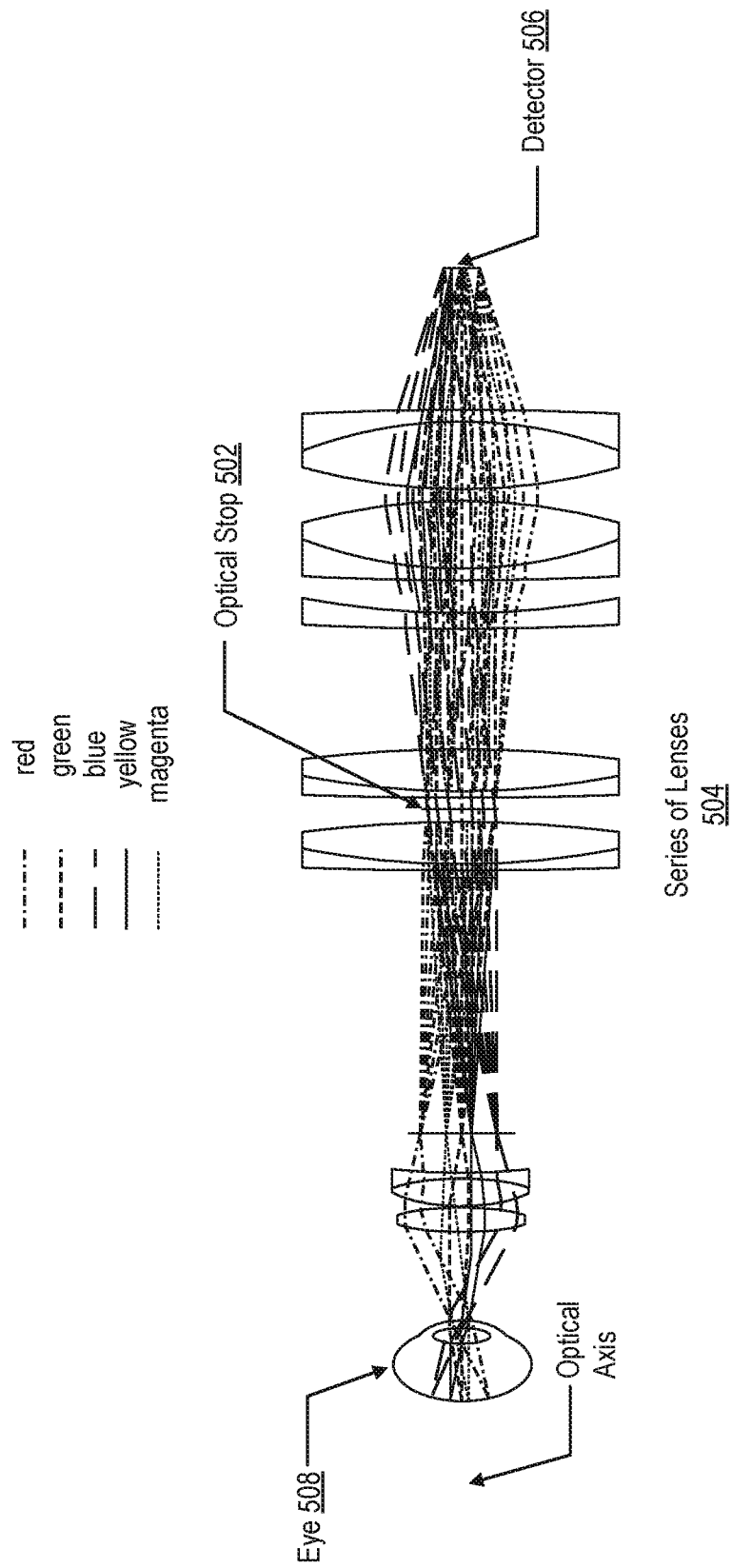
FIG. 5A depicts a retinal camera attempting to image the retina of an eye that has shifted downward by 1.5 millimeters (mm).

FIG. 5A depicts a retinal camera 500 attempting to image the retina of an eye 508 that has shifted downward by 1.5 mm. The retinal camera 500 can include an optical stop 502 interposed between a series of lenses 504 and a detector 506. As noted above, light rays reflected back into the retinal camera 500 by the retina will be guided through the series of lenses 504 toward the optical stop 502 and the detector 506. However, if the eye 508 shifts horizontally or vertically with respect to the optical axis and the optical stop 502 remains in its original location, the light rays will be displaced along the detector 506. Said another way, the light rays will be guided through the series of lenses 504 in such a manner that the light rays no longer fall upon the detector 506 in the same location as if the eye 508 were imaged in its original position.

Figure 5B:
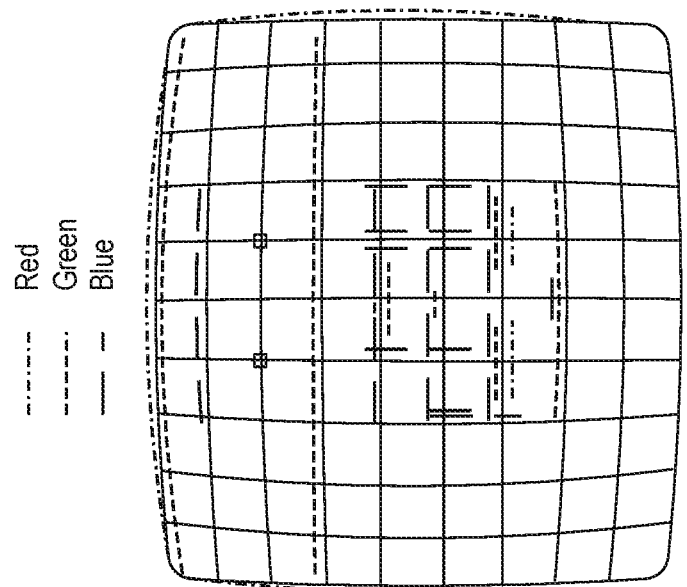
FIG. 5B shows how the downward shift of 1.5 mm has caused vignetting to occur in the image formed by the detector.

Small shifts in the position of the eye 508 can create noticeable changes in image quality. FIG. 5B, for example, shows how the downward shift of 1.5 mm has caused vignetting to occur in the image formed by the detector 506. Vignetting generally refers to the reduction of brightness or saturation at the periphery compared to the center of the image. Here, for instance, vignetting is apparent in the changes to the colors and contrast along the periphery of the image (e.g., in comparison to the image of FIG. 6B).

Figure 6A:
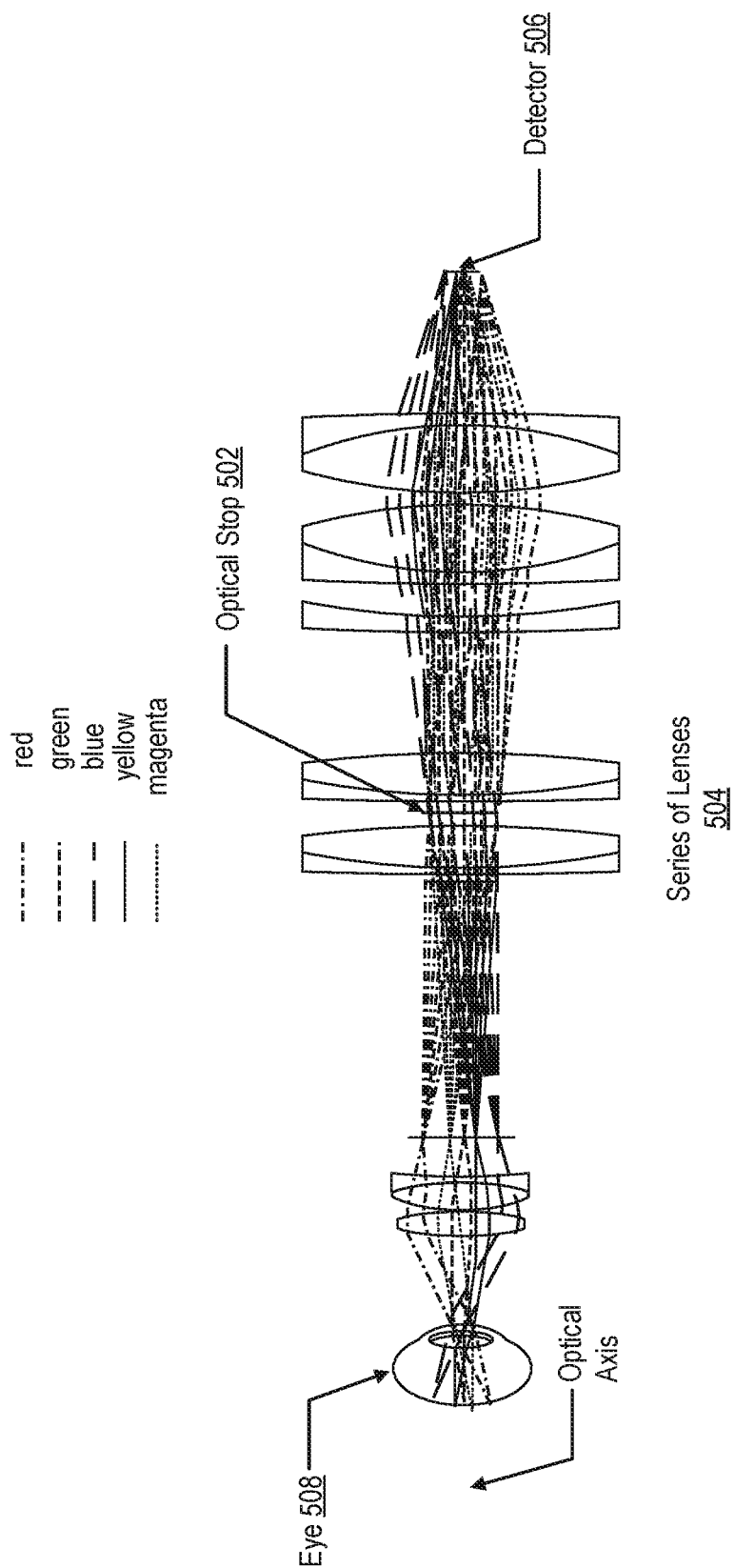
FIG. 6A depicts the retinal camera after the optical stop has been shifted downward to compensate for the downward shift of the eye.

FIG. 6A depicts the retinal camera 500 after the optical stop 502 has been shifted downward to compensate for the downward shift of the eye 508. As noted above, movement of the optical stop 502 may be proportional to movement of the eye 508. In fact, the relationship between eye shift and optical stop shift may be substantially linear (e.g., approximately two-to-one). Accordingly, the optical stop 502 may be shifted downward by approximately 0.75 mm to compensate for the downward shift of the eye 508 by 1.5 mm.

Figure 6B:
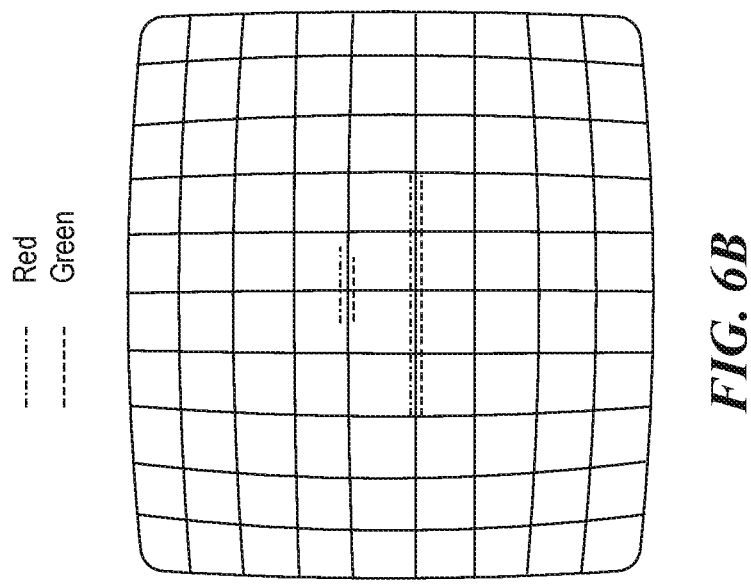
FIG. 6B shows how a corresponding shift in the optical stop can recover some of the light rays entering the retinal camera, and thus improve retinal image quality.

Such movement by the optical stop 502 enables the retinal camera 500 to recover retinal image quality as the eye 508 shifts. When the eye 508 is imaged along the optimal optical axis, light rays reflected back into the retinal camera 500 by the eye 508 will fall upon the detector 508 in one or more specified locations. Moving the optical stop 502 based on the eye shift causes the light rays to fall upon the detector 506 nearer the specified location(s) than would otherwise occur. FIG. 6B shows how a corresponding shift in the optical stop 502 can recover some of the light rays entering the retinal camera 500, and thus improve retinal image quality.

Figure 7:
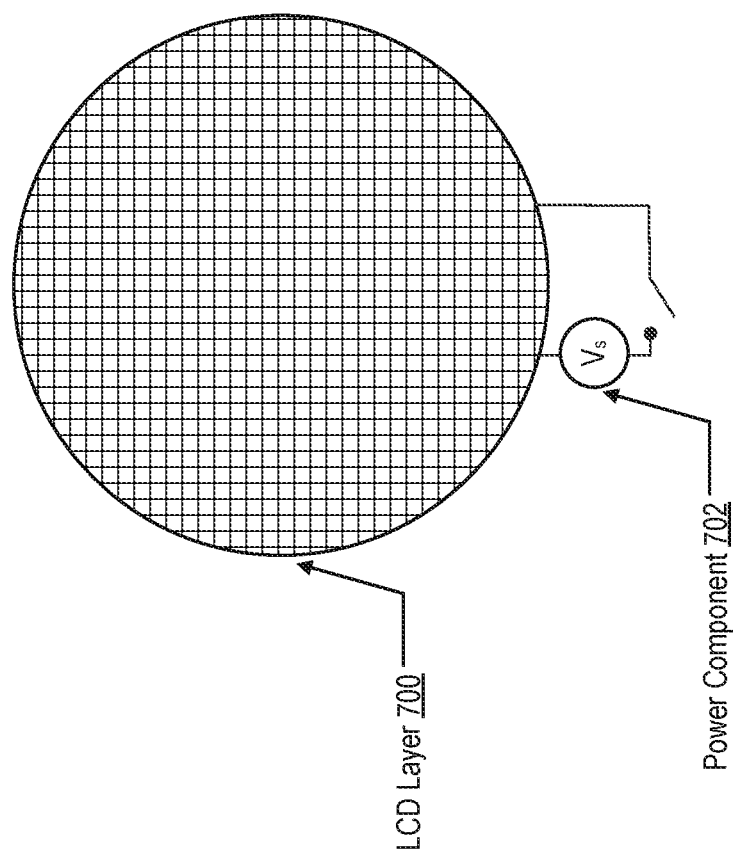
FIG. 7 depicts a pixelated liquid crystal display (LCD) layer having multiple pixels that are individually controllable.

FIG. 7 depicts a pixelated liquid crystal display (LCD) layer 700 having multiple pixels that are individually controllable. The LCD layer 700 may be electrically coupled to a power component 702 that is able to separately apply a voltage to each pixel to vary its transparency. Provisioning voltage in such a manner allows the power component 702 to digitally create an optical stop by changing which pixel(s) in the LCD layer 700 are active at a given point in time. Such action can be facilitated by one or more polarizing layers (also referred to as "polarizers") arranged within, or adjacent to, the LCD layer 700.

Changing the transparency of a pixel will allow light to pass through the corresponding segment of the LCD layer 700. For example, a segment of the LCD layer 700 that includes one or more pixels may appear substantially transparent when used as an optical stop. The remainder of the LCD layer 700 may appear partially or entirely opaque. To move the optical stop, the power component 702 may apply voltage(s) causing substantially transparent pixels to become substantially opaque and/or causing substantially opaque pixels to become substantially transparent.

Here, the LCD layer 700 is illustrated as a circle. However, those skilled in the art will recognize that the outer bounds of the LCD layer 700 could form another geometric shape. For example, other shapes (e.g., a square, rectangle, or ellipsoid) may be preferred based on the configuration of the retinal camera, the expected movement of the eye, the design of the digitally-created optical stop, etc.

Moreover, the LCD layer 700 could include any number of pixels. In some embodiments, the LCD layer 700 includes tens or hundreds of pixels. In such embodiments, the optical stop may be defined by multiple pixels (e.g., a four-by-four pixel segment). In other embodiments, the LCD layer 700 includes fewer pixels, though those pixels are often larger in size. For example, the LCD layer 700 may include four, six, or eight separately-controlled pixels. In such embodiments, the optical stop may be defined by a single pixel.

Note that other forms of pixelated display technologies may also be used, such as plasma display panels (PDPs). Thus, the LCD layer 700 could instead be a "variable transparency layer" able to alter its appearance in several different ways.

For example, the variable transparency layer may vary its opacity when a voltage is applied via polymer dispersed liquid crystal (PDLC) technology. Voltage can be used to change the position and orientation of liquid crystals disposed within a polymer matrix in order to allow more or less light to pass through the variable transparency layer. In such embodiments, the variable transparency layer can include electrically-conductive coatings (e.g., polyethylene terephthalate (PET)) on each side of a polymer matrix that includes randomly-arranged liquid crystals. When the power component 702 applies a voltage to the conductive coatings, the liquid crystals within the polymer matrix become aligned and the variable transparency layer becomes substantially or entirely transparent. However, when the power component 702 ceases to apply the voltage, the liquid crystals scatter and the variable transparency layer becomes substantially opaque or translucent.

As another example, the variable transparency layer may darken its appearance when a voltage is applied via electrochromism. Electrochromism enables some materials to reversible change opacity by using bursts of voltage to cause electrochemical redox reactions in electrochromic materials. In such embodiments, the variable transparency layer may include a first conducting oxide layer, an electrochromic layer (e.g., tungsten oxide ($WO_3$)), an ion conductor layer, an ion storage layer (e.g., lithium cobalt oxide ($LiCoO_2$)), and a second conducting oxide layer. The conducting oxide layers may be thin films of optically-transparent, electrically-conductive materials, such as indium tin oxide (ITO). The conducting oxide layers could also be composed of other transparent conductive oxides (TCOs), conductive polymers, metal grids, carbon nanotubes, graphene, ultrathin metal films, or some combination thereof. The ion conductor layer can include a liquid electrolyte or a solid (e.g., inorganic or organic) electrolyte. In such embodiments, the power component 702 (which is coupled to the conducting oxide layers) is able to selectively apply a voltage to either of the conducting oxide layers, which drives ions from the ion storage layer into the electrochromic layer and vice versa. An ion-soaked electrochromatic layer is able to reflect light, thereby enabling the variable transparency layer to appear at least partially opaque.

Electrochromic and PDLC techniques have been selected for the purpose of illustration. Other technologies that enable the modification of light transmission properties could also be used to achieve the same (or similar) effects, such as photochromic, thermochromic, suspended particle, and micro-blind techniques.

Figure 8:
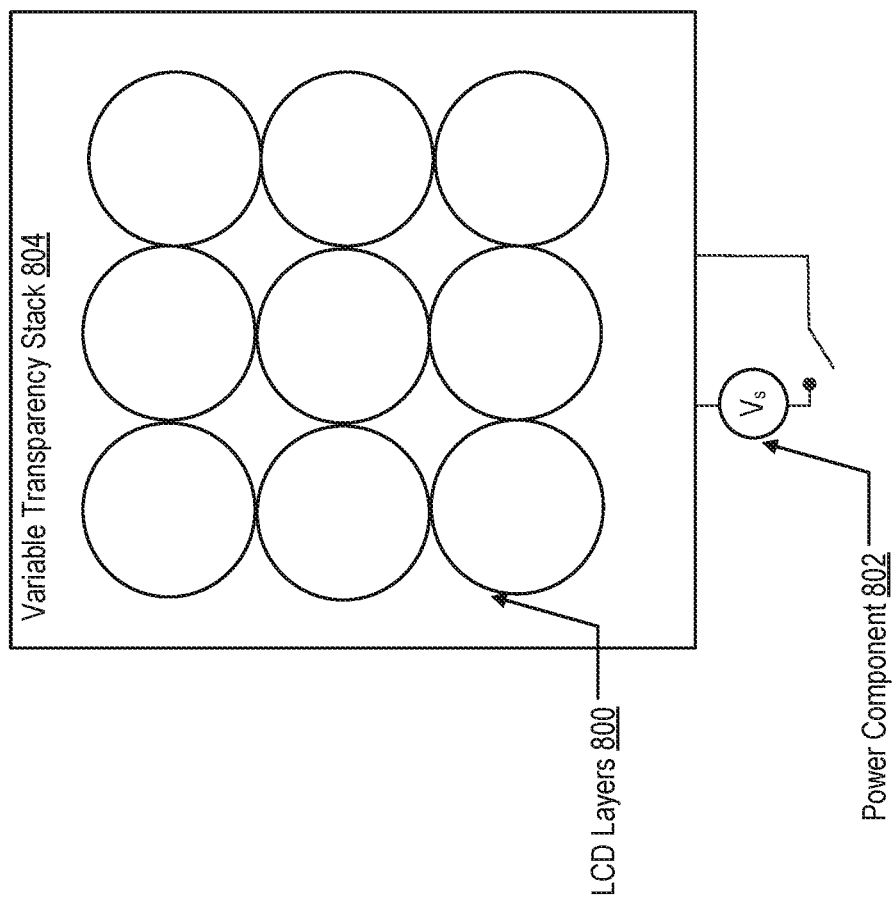
FIG. 8 depicts a variable transparency stack having multiple LCD layers that are individually controllable.

FIG. 8 depicts a variable transparency stack 804 having multiple LCD layers 800 that are individually controllable. As shown in FIG. 7, a single transparent LCD layer may have a periodic pattern that causes it to be pixelated. For example, a substrate (e.g., ITO) may be patterned with a grid of pixels that are separately controllable. However, unlike the pixelated LCD layer 700 of FIG. 7, each LCD layer of the multiple LCD layers 800 included in the variable transparency stack 804 is typically non-pixelated. Here, for example, a substrate (e.g., ITO) is patterned with a geometric shape (e.g., a circle) to form each LCD layer. But rather than pixelate the LCD layers 800, each LCD layer is instead separately connected to the power component 802 (e.g., using separate leads). This ensures that each LED layer can be controlled independently of the other LED layer(s).

The multiple LCD layers 800 can be connected to one another to form the variable transparency stack 804. As shown in FIG. 8, each LCD layer within the variable transparency stack 804 may be offset from the other LCD layers. In some embodiments, each of the LCD layers 800 partially overlaps at least one other LCD layer. The optical stop of the retinal camera can be moved by changing which LCD layer is active at a given point in time. Thus, the LCD layers 800 within the variable transparency stack 804 may be lit or unlit depending on the position of the eye being imaged.

The variable transparency stack 804 may include any number of LED layers 800. For example, embodiments may include four, six, eight, or ten LED layers. Moreover, the LED layers 800 within the variable transparency stack 804 may be of the same size and/or shape, or different sizes and/or shapes.

The outer bounds of the variable transparency stack 804 limit the possible positions of the optical stop. The arrangement of the LCD layers 800 (and thus the outer bounds of the variable transparency stack 804) may be based on factors influencing the optical design of the retinal camera as a whole, including the number, type, or placement of lenses (e.g., the lenses 304 of FIG. 3), the expected eye location, etc.

The variable transparency stack 804 can include the multiple LCD layers 800 and other layers (e.g., optically-clear adhesive layers). For example, optically-clear bonding layers may be used to bind the LCD layers 800 to one another. Each bonding layer can include an adhesive (e.g., an acrylic-based adhesive or a silicon-based adhesive). Moreover, each bonding layer is preferably substantially or entirely transparent (e.g., greater than 99% light transmission). The bonding layers may also display good adhesion to a variety of substrates, including glass, ITO, polyethylene (PET), polycarbonate (PC), polymethyl methacrylate (PMMA), etc.

An optical stop unit including the optical stop 302 of FIG. 3, the variable transparency stack 804 of FIG. 8, or the LCD layer 700 of FIG. 7 can be adapted for use within an ophthalmic imaging apparatus. For example, in some embodiments the optical stop unit includes a unit housing designed to fit within the ophthalmic imaging apparatus. Other components (e.g., the power component 702 of FIG. 7 or the power component 802 of FIG. 8) could also reside within the unit housing. Moreover, the optical stop unit may include a communication interface configured to receive a command from a controller of the ophthalmic imaging apparatus, and then select a voltage to apply based on the command. The voltage could cause servomotor(s) to move the optical stop 302 of FIG. 3, certain pixel(s) within the LCD layer 700 of FIG. 7 to become transparent, or certain layer(s) within the variable transparency stack 804 of FIG. 8 to become transparent.

FIG. 9 depicts a flow diagram of a process 900 for recovering retinal image quality as a subject shifts their eye during the imaging process. Initially, the subject places an eye proximate to the objective lens of a retinal camera (step 901). The subject will typically sit near the retinal camera with their chin set within a chin rest and their forehead pressed against a bar.

The retinal camera can then determine the location of the eye being imaged by the retinal camera (step 902). As noted above, several different mechanisms may be used to establish the location of the eye (and, more specifically, the iris). For example, infrared light source(s) may be configured to project infrared beam(s) into the visible light illumination path of the retinal camera. Because the iris will generally not constrict when illuminated by infrared light, a live view of the retina can be captured and used to establish the position of the eye. As another example, the retinal camera may capture retinal images with the retinal stop located at different positions. Image processing algorithm(s) may be applied to the retinal images to determine whether the retina has been captured in any of the retinal images.

After determining the location of the eye, the retinal camera can set the position of the optical stop (step 903). The position of the optical stop can be set manually or automatically. For example, a retinal photographer may visually observe the imaging light rays produced by the retinal camera (e.g., via a telescopic eyepiece) and alter the position of the optical stop using indexing wheel(s), joystick (s), etc. As another example, the retinal camera may instruct servomotor(s) to alter the position of the optical stop responsive to adjustments specified by software executing on the retinal camera or another computing device communicatively coupled to the retinal camera.

The retinal camera can then generate a retinal image from light rays reflected into the retinal camera by the eye (step 904). Such action may be prompted by the retinal photographer pressing a shutter release that causes the retinal image to be captured.

In some embodiments, the retinal camera continually or periodically monitors the position of the eye (step 905). The retinal camera may use the same tracking mechanism used to initially determine the location of the eye or a different tracking mechanism. For example, the retinal camera may use a higher-resolution tracking mechanism to continually monitor the position of the eye so that small variations (e.g., those less than one mm) can be consistently detected.

Responsive to determining that the position of the eye has changed, the retinal camera can modify the position of the optical stop (step 906). The optical stop may be automatically moved without requiring input from the retinal photographer or the subject. For example, the retinal camera may once again instruct the servomotor(s) to alter the position of the optical stop responsive to adjustments specified by the software executing on the retinal camera or another computing device communicatively coupled to the retinal camera. Thus, the subject may be able to look into the retinal camera without being concerned about alignment of the eye and the optical stop. Instead, the retinal camera could automatically determine the location of the eye and move the optical stop accordingly.

Unless contrary to physical possibility, it is envisioned that the steps described above may be performed in various sequences and combinations. For example, the retinal camera may automatically generate a retinal image from light rays reflected into the retinal camera by the eye each time the position of the optical stop is modified. Other steps may also be included in some embodiments.

Processing System

Figure 10:
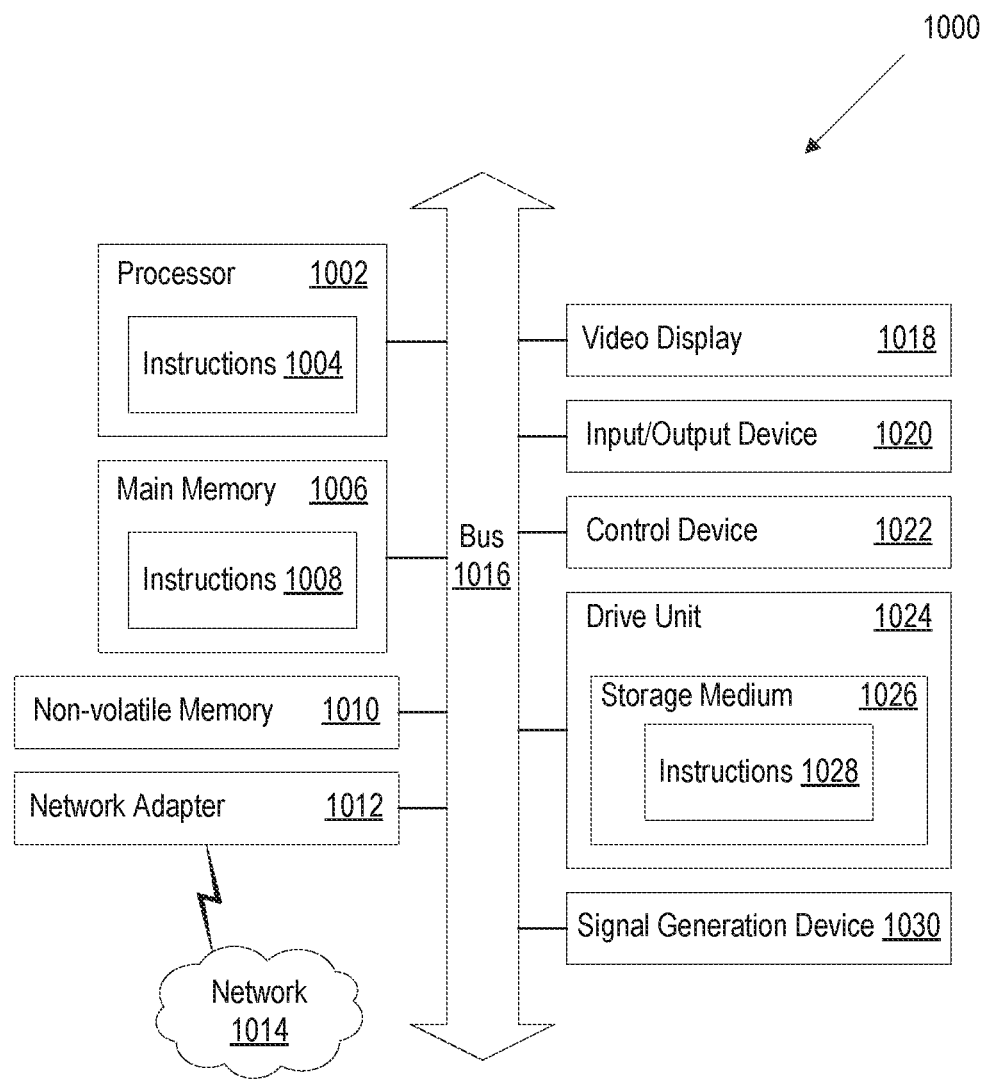
FIG. 10 is a block diagram illustrating an example of a processing system in which at least some operations described herein can be implemented.

FIG. 10 is a block diagram illustrating an example of a processing system 1000 in which at least some operations described herein can be implemented. For example, some components of the processing system 1000 may be hosted on a retinal camera (e.g., retinal camera 300 of FIG. 3), while other components of the processing system 1000 may be hosted on a computing device that is communicatively coupled to the retinal camera. The computing device may be connected to the retinal camera via a wired channel or a wireless channel.

The processing system 1000 may include one or more central processing units ("processors") 1002, main memory 1006, non-volatile memory 1010, network adapter 1012 (e.g., network interface), video display 1018, input/output devices 1020, control device 1022 (e.g., keyboard and pointing devices), drive unit 1024 including a storage medium 1026, and signal generation device 1030 that are communicatively connected to a bus 1016. The bus 1016 is illustrated as an abstraction that represents one or more physical buses and/or point-to-point connections that are connected by appropriate bridges, adapters, or controllers. The bus 1016, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1000 may share a similar computer processor architecture as that of a desktop computer, tablet computer, personal digital assistant (PDA), mobile phone, game console (e.g., Sony PlayStation® or Microsoft Xbox®), music player (e.g., Apple iPod Touch®), wearable electronic device (e.g., a watch or fitness band), network-connected ("smart") device (e.g., a television or home assistant device), virtual/augmented reality systems (e.g., a head-mounted display such as Oculus Rift® or Microsoft Hololens®), or another electronic device capable of executing a set of instructions (sequential or otherwise) that specify action(s) to be taken by the processing system 1000.

While the main memory 1006, non-volatile memory 1010, and storage medium 1026 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1028. The term "machine-readable medium" and "storage medium" shall also be taken to include any medium that is capable of storing, encoding, or carrying a set of instructions for execution by the processing system 1000.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1004, 1008, 1028) set at various times in various memory and storage devices in a computing device. When read and executed by the one or more processors 1002, the instruction(s) cause the processing system 1000 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1010, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1012 enables the processing system 1000 to mediate data in a network 1014 with an entity that is external to the processing system 1000 through any communication protocol supported by the processing system 1000 and the external entity. The network adapter 1012 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1012 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. An imaging apparatus comprising:
a light source configured to emit light during an imaging process;
an objective lens (i) through which the light exits the imaging apparatus for illumination of a retina of an eye and (ii) at which to collect light reflected by the eye;
an internal lens having an optical axis defined therethrough along which the reflected light is directed toward a capturing medium;
an optical stop controllably positionable along a vertical plane between the internal lens and the capturing medium,
wherein the vertical plane intersects but is substantially orthogonal to the optical axis of the internal lens;
a mechanism operable to reposition the optical stop along the vertical plane in an automated manner without requiring input from an operator; and
a controller, coupled to the mechanism, configured to adaptively reposition the optical stop responsive to a determination that the eye has moved during the imaging process, so as to align the optical stop with the eye without moving the imaging apparatus, thereby ensuring that the reflected light that passes through the optical stop falls on the capturing medium.

2. The imaging apparatus of claim 1, wherein the mechanism includes a servomotor, a cam mechanism, a stepper motor, a pneumatic actuator, a piezoelectric actuator, a voice coil, or any combination thereof.

3. The imaging apparatus of claim 1, further comprising an eye tracker, wherein the controller is further configured to:
determine, based on an output of the eye tracker, whether a spatial adjustment of the eye has caused a path along which the reflected light travels to move during the imaging process.

4. The imaging apparatus of claim 1, wherein the controller is further configured to:
determine an amount of movement caused by a spatial adjustment of the eye during the imaging process,
wherein a specified location to which the optical stop is repositioned by the mechanism corresponds to the determined amount.

5. The imaging apparatus of claim 1, further comprising:
an infrared light source configured to direct infrared light into the eye.

6. The imaging apparatus of claim 5, wherein the controller is further configured to:
analyze a live view of the retina to identify a spatial position of the eye, wherein the live view of the retina is created from infrared light reflected by the eye into the imaging apparatus,
generate an instruction responsive to identifying the spatial position of the eye, and
transmitting the instruction to the mechanism, which prompts the mechanism to position the optical stop in a specified location that enables the imaging apparatus to produce a retinal image having a higher resolution than otherwise possible before the optical stop is adaptively repositioned.

7. The imaging apparatus of claim 1, wherein the controller is further configured to:
retrieve multiple retinal images produced by the imaging apparatus,
wherein each retinal image of the multiple retinal images corresponds to a different optical stop location,
analyze the multiple retinal images to identify a particular retinal image having the best image quality,
wherein image quality is based on brightness level, whether vignetting is present, modulation transfer function (MTF) quality, or any combination thereof,
generate an instruction responsive to identifying the particular retinal image, and
transmitting the instruction to the mechanism, which prompts the mechanism to position the optical stop in a specified location corresponding to the particular retinal image.

8. The imaging apparatus of claim 1, wherein the capturing medium is film, a digital charge-coupled device (CCD), or a complementary metal-oxide-semiconductor (CMOS).

9. A method for recovering retinal image quality responsive to eye movements during an imaging process, the method comprising:
determining, by an ophthalmic imaging apparatus, a location of an eye being imaged by the ophthalmic imaging apparatus;
positioning, by the ophthalmic imaging apparatus, an optical stop that collects light traveling along a path toward a capturing medium for purposes of imaging the eye at a specified location along a vertical plane that corresponds to the determined location,
wherein the vertical plane intersects but is substantially orthogonal to the path;
monitoring, by the ophthalmic imaging apparatus, the location of the eye while the ophthalmic imaging apparatus is imaging; and
responsive to a determination that the location of the eye has changed,
automatically moving, by the ophthalmic imaging apparatus, the optical stop to a new location along the vertical plane that corresponds to the location of the eye, so as to align the optical stop with the eye without moving the ophthalmic imaging apparatus.

10. The method of claim 9, further comprising:
producing, by the ophthalmic imaging apparatus, a retinal image from the light guided through the optical stop toward the capturing medium,
wherein the light is reflected into the ophthalmic imaging apparatus by the eye.

11. The method of claim 9, wherein said monitoring is performed continually or periodically throughout the imaging process.

* * * * *